United States Patent [19]

DeMarco

[11] Patent Number: Plant 7,069

[45] Date of Patent: Dec. 12, 1989

[54] PEACH TREE NAMED LADY NANCY

[76] Inventor: Medio DeMarco, 325 N. White Horse Pike, Hammonton, N.J. 08037

[21] Appl. No.: 296,691

[22] Filed: Jan. 13, 1989

[51] Int. Cl.[4] ..... A01H 5/00
[52] U.S. Cl. ..... Plt./42
[58] Field of Search ..... Plt./42

*Primary Examiner*—James R. Feyrer

*Attorney, Agent, or Firm*—Frank B. Robb

[57] ABSTRACT

A new peach tree variety which originated as a natural limb mutation of the cultivar 'Jerseyqueen', producing late maturing, large, globose to ovate, very firm fruit, having a strong red skin color, with white flesh and a yellow suture line just under the skin, long storage life, slow softening flesh, the tree being large, very vigorous, and moderately productive.

1 Drawing Sheet

GENERAL DESCRIPTION OF THE INVENTION

My new variety of peach tree, originated in an orchard which is under my direction and which produces peaches of various varieties for commercial purposes, and was discovered by me as natural limb mutation of the cultivar 'Jerseyqueen'.

It was discovered in my orchard in which the "Jerseyqueen" variety has long been grown, in the area near Hammonton, N.J.

Observations of the tree and of the fruit produced were carried on by me for a substantial period of time over growing seasons and as a result, I have caused the same to be propagated because of its very firm white flesh, excellent quality and similarties to 'Jerseyqueen' which is a popular variety in New Jersey.

I have produced a block of trees of my new variety asexually by budding, so that a further evaluation could be carried on and after this evaluation, because of the quality, slow softening of the flesh, and season of maturity, along with the flavor and white flesh color, having a noticeable yellow suture line, and characteristics like 'Jerseyqueen', the variety will now be introduced to the trade and known as 'Lady Nancy' for commercial purposes.

The trees of my new variety have exhibited a strong, very vigorous growth habit, with moderate winter hardiness, together with the ability to produce large globose to ovate, very firm fruit, with a strong red skin coloration.

The fruit flesh, is white as stated, with slow softening characteristics, and a very good fruit flavor. The flesh further has the unusual characteristic of an orange line just under the skin along the suture all the way to the pit.

The fruit ripens late in the season for five to seven days before the variety 'Rio Oso Gem' (U.S. Pat. No. P.P. 84) and with the variety 'Jerseyqueen'.

My new variety 'Lady Nancy' is distinctly different then 'Jerseyqueen' having the white flesh and strong red skin color and a dark pinkish undercolor, while the 'Jerseyqueen' is of the yellow flesh, scarlet red skin color type, with yellowish red under color.

As before stated the asexual reproduction of my new variety which I have carried on, has demonstrated that the combination of characteristics described, comes true and is established and transmitted from generation to generation.

The specimen described was observed near Hammonton, N.J.

DETAILED DESCRIPTION OF THE INVENTION

The illustration as shown in the drawing provided herewith, shows typical specimens of the fruit and foliage of my new variety depicted in color as nearly true as is possible to make the same in photographic color illustration of this kind, noting that all references to color where definable are made by using the disclosure of the Nickerson Color Fan produced by the Munsell Color Company.

Dates of first and last pickings: Aug. 25 to Sept. 5.

Tree: Large size, very vigorous, open, spreading, vase shaped Moderately hardy and productive, regular bearer.

- *Trunk.*—Medium stocky; medium smooth.
- *Branches.*—Stocky; medium smooth; brownish; dull.
- *Leaves.*—Acutely pointed; medium thick; smooth. Length — approximately 6½ inches Width — about 1½ inches. Color — Moderate green 7.5 G 4/7. Margin—crenate. Petioles—medium long and medium thick. Glands—average number 3, opposite, small, reniform and appressed.

Flowers:

- *Date of first blossom.*—Early — Apr. 1.
- *Size.*—Large, showy.
- *Color.*—Deep pink 2.5 R 6/11.

Fruit:

- *Maturity when described.*—Hard — Aug. 29.
- *Size.*—Large to very large-axial diameter about 2⅞ inches to 3⅛ inches; at right angles to suture plane— approximately 2¾ inches to 3½ inches.
- *Form.*—Variable, unsymmetrical, globose to ovate.
- *Suture.*—Distinct, extends from base to apex over half of the circumference.
- *Ventral surface.*—Rounded, slightly ridged on either side.
- *Cavity.*—Rounded, abrupt, generally circular, somewhat elongated. Depth — ½ inch. Breadth — ½ inch. Markings — whitish green.
- *Base.*—Recuse.
- *Apex.*—Pointed.
- *Stem.*—Short, stout, weak.

*Skin.*—Medium, free. Color — Blushed to mottled red. Approximately 65% to 75% of skin is strong red 2.5 R 5/2; and approximately 25% to 35% greenish white on the portion not exposed to the sun.

Flesh:

Color.—White with a yellow streak along the suture line just under the skin.

*Amygladin.*—Scant.

*Fibres.*—Few. Ripens fairly evenly with a mild delicate flavor.

*Aroma.*—Distinct.

*Eating quality.*—Best.

Stone: Free.

*Fibres.*—Parts from flesh smoothly.

*Size.*—Large.

*Form.*—Apex acuminate.

*Base.*—Hilum, oval.

*Sides.*—Unequal.

*Surface.*—Pitted to furrowed throughout.

Keeping quality: Excellent, slow softening. Good insect resistance. Good disease resistance. Excellent shipping quality.

I claim:

1. A new and distinct variety of peach tree, substantially as herein shown and described, characterized particularly as to novelty by the unique combination of large size, very vigorous, open, spreading, vase shaped, regular bearing tree, producing freestone fruit having white flesh with a yellow suture line, moderate winter hardiness and greater firmness than other white peaches, providing excellent shipping quality, superior flavor and earlier ripening than the variety 'Rio Oso Gem'.

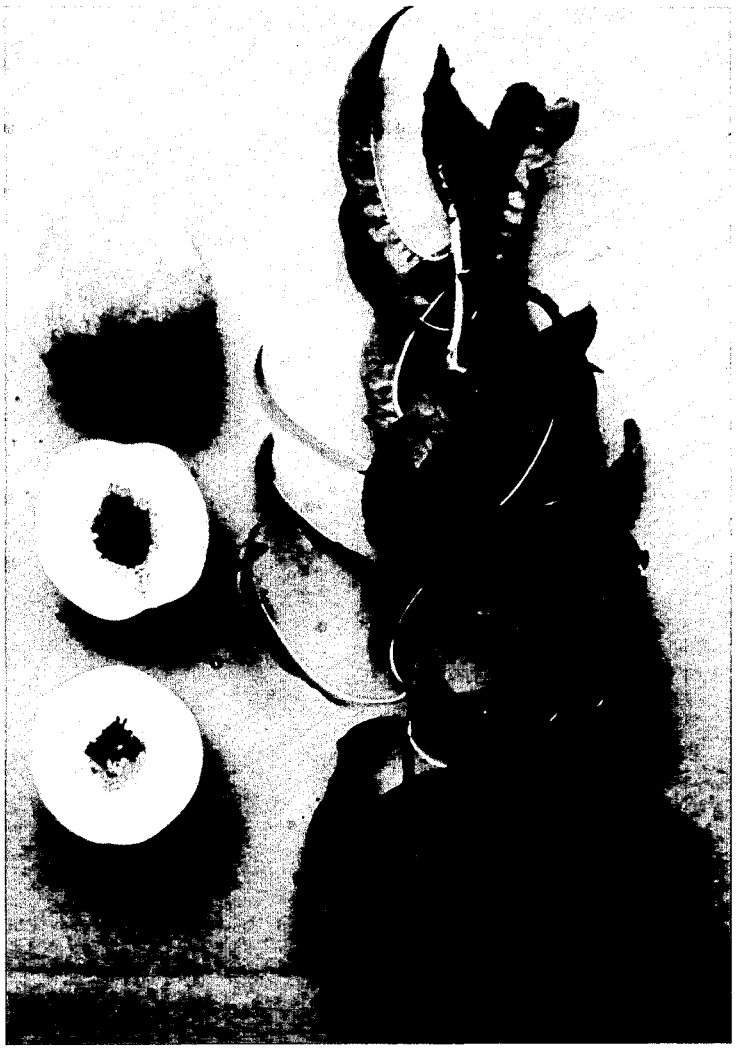

* * * * *